(12) United States Patent
Woodward

(10) Patent No.: US 7,125,836 B2
(45) Date of Patent: Oct. 24, 2006

(54) METHOD OF CANCER SCREENING; METHOD OF CANCER TREATMENT; AND METHOD OF DIABETES TREATMENT

(75) Inventor: John R. Woodward, Dallas, TX (US)

(73) Assignee: Les Medecins L.P., Dallas, TX (US)

( * ) Notice: Subject to any disclaimer, the term of this patent is extended or adjusted under 35 U.S.C. 154(b) by 0 days.

(21) Appl. No.: 11/133,838

(22) Filed: May 19, 2005

(65) Prior Publication Data

US 2006/0062757 A1   Mar. 23, 2006

Related U.S. Application Data

(63) Continuation of application No. 11/032,399, filed on Jan. 10, 2005, now abandoned, which is a continuation-in-part of application No. 10/946,213, filed on Sep. 21, 2004.

(51) Int. Cl.
*A01K 61/00* (2006.01)
*A61K 38/43* (2006.01)
*A61K 39/00* (2006.01)

(52) U.S. Cl. ............. 514/1; 424/94.1; 424/184.1

(58) Field of Classification Search ............... 514/1; 424/94.1, 184.1
See application file for complete search history.

(56) References Cited

OTHER PUBLICATIONS

Testerman et al (Journal of Leukocyte Biology, 1995, 58:365-372).*
VALTREX™ caplets prescribing information, GlaxoSmithKline).*
Diaz-Arrastia et al. (Clinical Cancer Research, 2001, 7: 3031-3033).*
Gura (Science, v278, 1997, pp. 1041-1042).*
Recent papers showing the effect of TNF-alpha and NF-kB interruption on different autoimmune diseases; Autoimmune Disease Research Foundation.
Gura et al. Science, 1997. 278: 1041-1042.
Diaz-Arrastia et al. Clinical Cancer Research , 2001.7:3031-3033.
VALTREX Caplets Prescribing Information, GlaxoSmithKline.

* cited by examiner

*Primary Examiner*—Jeffrey Siew
*Assistant Examiner*—Sean E Aeder
(74) *Attorney, Agent, or Firm*—Michael A. O'Neil

(57) ABSTRACT

A method of cancer screening comprising the steps of administering the Blood CA 27,29 testing procedure; if the result is positive administering a mammogram; if the result is positive administering a needle biopsy; if the result is positive administering a PET scan; if the result is positive administering a blood tumor cell count. If all of the foregoing steps are positive, the cancer is treated by applying imiquimod transdermally to rotating sites, preferably by mixing ALDARA (TM) (imiquimod) 5% cream with an equal amount of H base cream (TM); administering a vaccine that induces production of tumor necrosis factor, preferably the BCG vaccine; and orally administering Valtrex (TM) (valacyclovir) twice daily. The foregoing treatment method is also effective in treating Type I diabetes, MS, and other epidermal cancers.

5 Claims, 3 Drawing Sheets

METHOD OF CANCER SCREENING; METHOD OF CANCER TREATMENT; AND METHOD OF DIABETES TREATMENT

CROSS-REFERENCE TO RELATED APPLICATIONS

This application is a continuation application of U.S. application Ser. No. 11/032,399 filed Jan. 10, 2005 (our file 120175-1005), now abandoned, which is a continuation-in-part application of U.S. application Ser. No. 10/946,213 filed Sep. 21, 2004, currently pending.

TECHNICAL FIELD

This invention relates generally to the detection and treatment of cancers, and more particularly to a method of screening for and a method of treating duct cell cancer of the breast, squamous cell cancer of the uterine cervix, anal cancer, diabetes, and multiple sclerosis.

BACKGROUND AND SUMMARY OF THE INVENTION

As is well known, various technologies are available to the medical profession for use in determining the presence of cancers in patients. Included are x-ray studies, magnetic resonance imaging (MRI) studies, CT scans, as well as studies of various body fluids such as blood, urine, etc. Potential sites for colon cancer, for example, can be investigated utilizing electro-optical technologies. In some cases needle biopsy or exploratory surgery is necessary to confirm either the presence or absence of suspected cancer.

Various techniques for treating cancers are also well known. Certain cancers can be surgically removed, whereas other cancers require radiation therapy, chemotherapy, or combinations of radiation therapy and chemotherapy. Other cancers are susceptible to control using one or more drug therapies.

Type I diabetes is generally diagnosed in juveniles and young adults. In type I diabetes, the pancreas does not make insulin, which is necessary for the body to process sugars. Persons with Type I diabetes can live long, healthy lives, but must be careful with their diet and must take insulin to manage their blood glucose levels. Currently, the only treatment for Type I diabetes is to take insulin, or receive pancreas or islet cell transplants.

Multiple sclerosis (MS) is a chronic, unpredictable disease of the nervous system that afflicts over 2.5 million persons worldwide. An MS attack destroys myelin, the protective fibers around nerve fibers in the central nervous system. The destroyed myelin is replaced by scars of hardened "sclerotic" tissue, and some nerve endings are permanently severed. The common symptoms are loss of balance, fatigue, poor circulation, slurred speech, blindness, and in some cases paralysis. Currently, the only treatment is disease-modifying drugs, including drugs with a chemotherapeutic agent. These treatments only modify the disease to lessen the severity or frequency of the MS attacks.

The present invention comprises a method of cancer screening, a method of cancer treatment, a method for treatment of diabetes, and a method for treatment of multiple sclerosis which has proven successful in controlling epidermal cancers including, but not limited to, duct cell breast cancer, cervical squamous cancer, and anal cancer, controlling Type I diabetes, and controlling multiple sclerosis. In accordance with the broader aspects of the invention, a method of cancer screening involves a series of testing procedures each more expensive than the one before. Only when results of each of the testing procedures are positive is the presence of cancer confirmed. The invention further comprises a method of treating cancer and insulin dependent Type I diabetes wherein the drug imiquimod is administered transdermally in conjunction with a vaccine that induces production of tumor necrosis factor, for example the BCG vaccine, and valacyclovir hydrochlorine tablets. The method of the present invention treats Type I diabetes by enabling the body to regenerate islet cells. Similarly, multiple sclerosis is managed and treated by enabling the body to repair nerve endings and regenerate damaged fibers.

BRIEF DESCRIPTION OF THE DRAWING

A more complete understanding of the present invention may be had by reference to the following Detailed Description when taken in connection with the accompanying Drawings, wherein.

DETAILED DESCRIPTION

Introduction

The following examples describe a method of detecting and treating duct cell breast cancer, and a method for treating Type I diabetes. However, the present invention is equally applicable to other epidermal cancers, such as squamous cancer of the uterine cervix and anal cancer, and the treatment of and management of multiple sclerosis.

EXAMPLE

Figure 1:
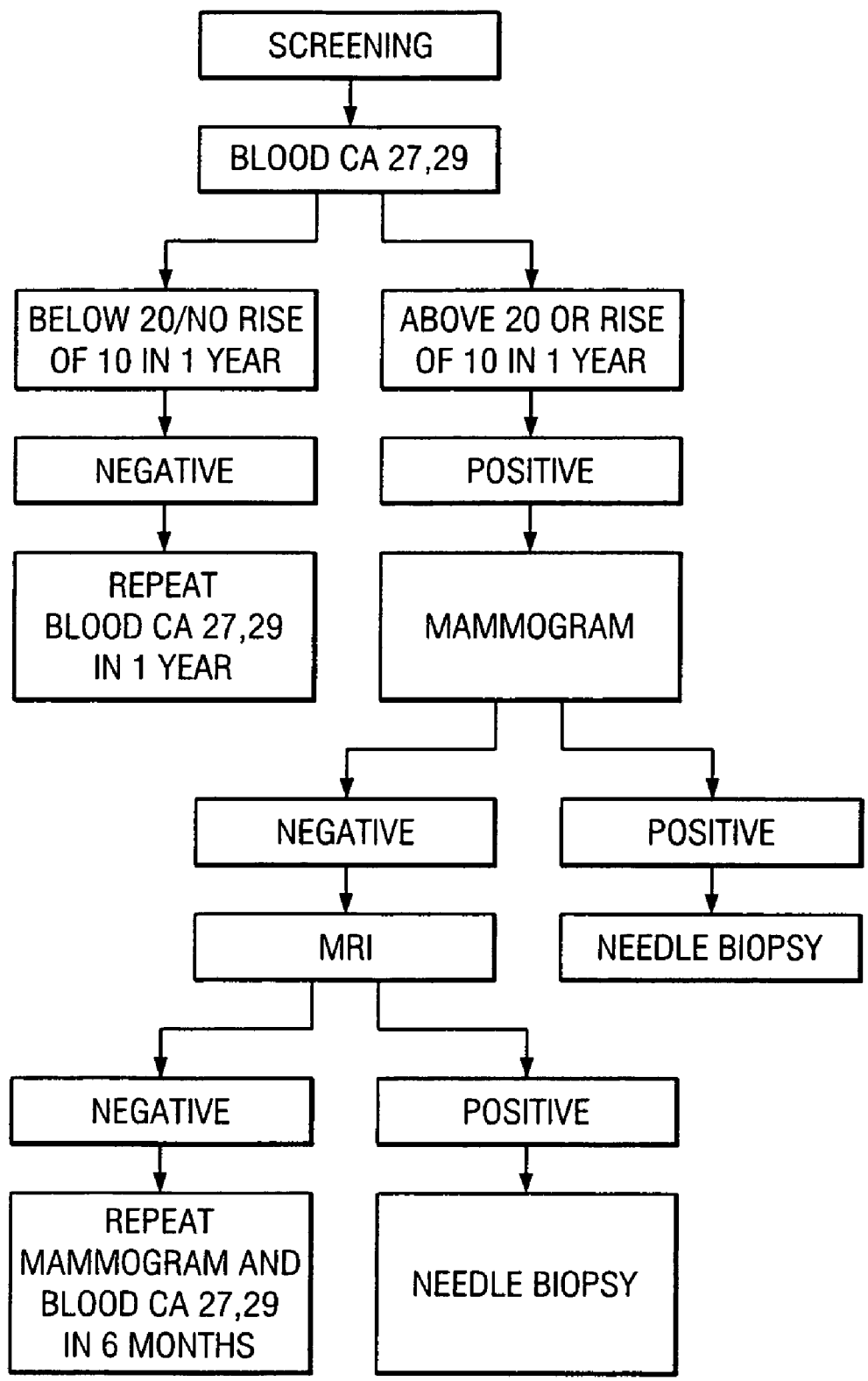
FIG. 1 is a flowchart illustrating initial steps in the cancer screening method of the present invention.

Referring to the Drawings, and particularly to FIG. 1 thereof, the early steps in the method of cancer screening of the present invention are shown therein. Screening begins with administration of the testing procedure known as Blood CA 27,29. The Blood CA 27,29 testing procedure has heretofore been utilized in monitoring the results of existing cancer treatment procedures. However, the Blood CA 27,29 procedure has not heretofore been used for cancer screening.

If the number comprising the results of the Blood CA 27,29 procedure is less than 20, and if there has been no increase in the number comprising the result of the Blood CA 27,29 testing procedure of ten (10) or more in the immediately preceding year, the result of the Blood CA 27,29 testing procedure is considered to be negative. The patient is then scheduled for follow-up testing utilizing the Blood CA 27,29 procedure in one year.

If the number comprising the result of the Blood CA 27,29 procedure is 20 or above, or if there has been an increase of 10 or more in the number comprising the result of the CA 27,29 testing procedure in the immediately preceding year, the result of the Blood CA 27,29 procedure is considered to be positive. In that event a mammogram testing procedure is administered. If the result of the mammogram testing procedure is negative, an MRI testing procedure is administered. If the result of the MRI testing procedure is negative, both the mammogram testing procedure and the Blood CA 27,29 testing procedure are re-administered in six months time. Conversely, if either the mammogram testing procedure is positive or the MRI testing procedure is positive, a needle biopsy of the identified lesion is performed.

Figure 2:
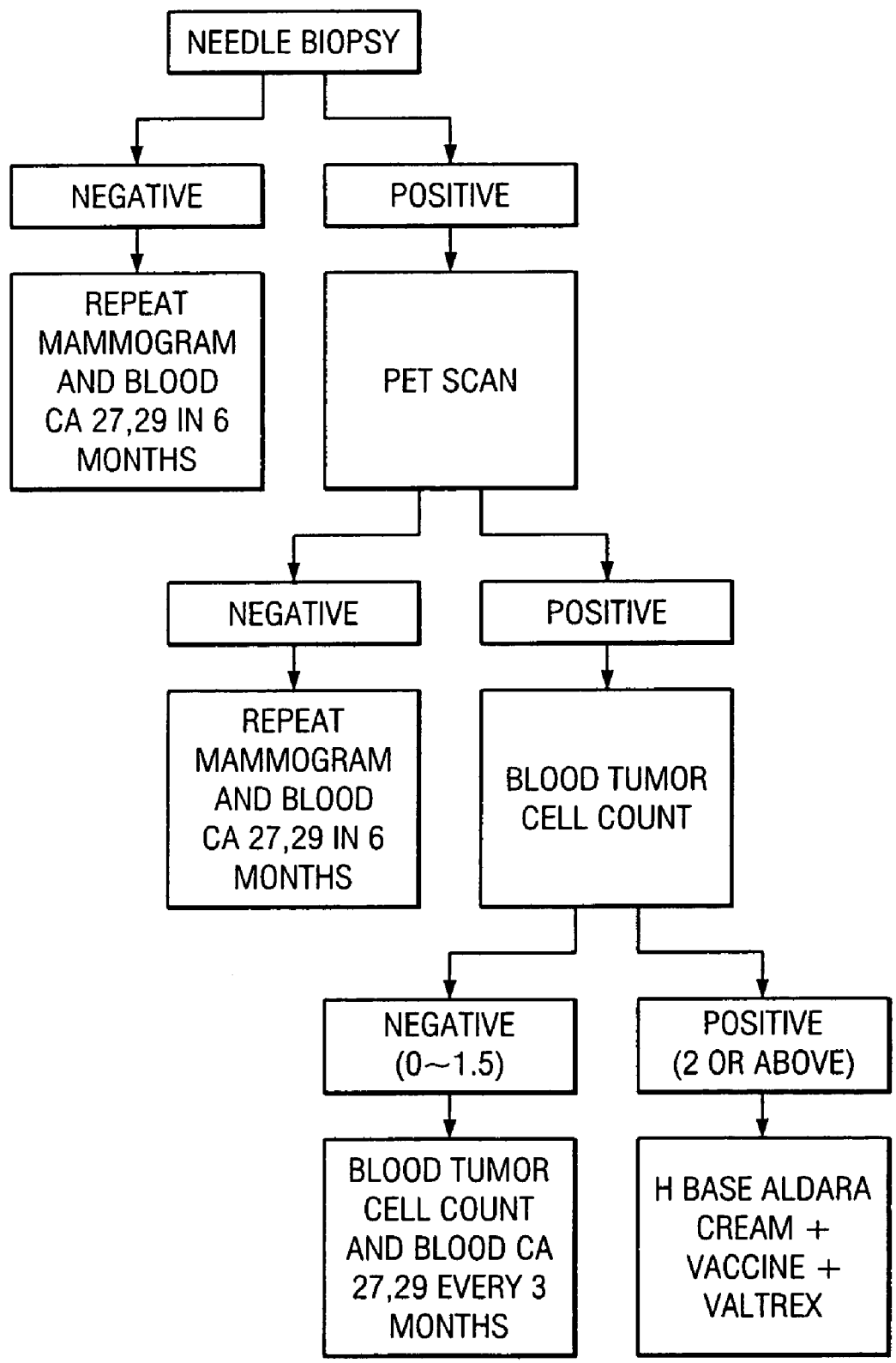
FIG. 2 is a flowchart illustrating subsequent steps in the cancer screening method of the present invention.

Referring to FIG. 2, if the results of the needle biopsy testing procedure are negative, both the mammogram testing procedure and the Blood CA 27,29 testing procedure are re-administered in six months. If the needle biopsy testing procedure is positive, a positron emission tomography (PET) scan testing procedure is administered. If the result of the PET scan testing procedure is negative, the mammogram testing procedure and the Blood CA 27,29 testing procedure are re-administered in six months. If the result of the PET scan testing procedure is positive, a blood tumor cell count testing procedure is administered. If the result of the blood tumor cell count testing procedure is negative, that is, if the number comprising the result of the blood tumor cell count testing procedure is between 0 and 1.5, the blood tumor cell count testing procedure and the Blood CA 27,29 testing procedure are administered at three month intervals. Conversely, if the blood tumor cell count testing procedure is positive, that is, if the number comprising the result of the blood tumor cell count testing procedure is two or above, the cancer treatment procedure of the present invention is administered.

The cancer treatment procedure of the present invention comprises the transdermal administration of the drug imiquimod combined with a vaccine that induces production of tumor necrosis factor and administration of valacyclovir hydrochiorine tablets. Imiquimod is commercially available from 3M Pharmaceuticals under the trademark ALDARA (TM) (imiquimod). A healthy human body produces the protein interferon alpha in response to an infection. Interferon alpha works to coat the infection or virus in order to make the infection or virus vulnerable to the human immune system. Imiquimod cream induces the production of interferon alpha once inside the human body, providing the needed interferon alpha not adequately produced by the patient's own body. In accordance with the present invention, ALDARA (TM) (imiquimod) cream 5% is mixed at a 1:1 ratio with H base cream. The ingredients of H base cream are:

water, glycerin, canola oil, stearic acid, cetyl alcohol, PEG-100 stearate, glyceryl stearate, dimethicone, magnesium aluminum silicate, propylene glycol, triethanolamine, polysorbate 60, xanthan gum, bitter almond kernel oil, aloe vera, grape seed extract, wheat germ oil, vitamin E acetate, vitamin A palmitate, Vitamin C palmitate, tetrasodium EDTA, potassium sorbate, diazolidinyl urea. H base cream is a proprietary product produced by Professional Compounds Centers of America and licensed by it.

The mixture of imiquimod and H base cream as described above is administered transdermally, preferably by mixing ¼ cc ALDARA (TM) (imiquimod) 5% cream with ¼ cc H base cream and applying the resulting mixture to various locations, i.e., the inner thigh, abdomen, hip, arms, etc., of the patient. Various sites of administration prevent any possible skin irritation. The foregoing amount of the mixture of ALDARA (TM) (imiquimod) 5% cream and H base cream is applied daily.

Tumor necrosis factor (also called TNFa, cachexin, or cachetin) stimulates T-cells that coordinate the immune system. In a healthy human body, tumor necrosis factor is released by white blood cells and other tissues in response to damage caused by an infection. Tumor necrosis factor is found in several vaccines. The preferable vaccine to be used in accordance with the present invention is the BCG vaccine, which is a common vaccine for tuberculosis, given in the United States and around the world. The tumor necrosis factor produced by the BCG vaccine and imiquimod work together to stimulate the T-cells and coordinate and improve the patient's immune system. Interferon alpha coats the virus or infection in order to make the virus or infection vulnerable to the tumor necrosis factor.

In accordance with the present invention, the vaccine is given in doses of 0.1 mL (100 µg) once every three weeks as long as the treatment continues. Valacyclovia hydrochlorine tablets, available from GlaxoSmithKline under the trademark VALTREX (TM) (valacyclovir) is a drug commonly used in the treatment for genital herpes. In accordance with the present invention, VALTREX (TM) (valacyclovir) tablets are consumed twice daily in 500 mg doses. The combination of the ALDARA (TM) (imiquimod) and H base cream, the BCG vaccination, and the VALTREX (TM) (valacyclovir) tablets is administered until a blood tumor cell count indicates that there are no cancer cells in the blood and a subsequent blood tumor cell count verifies a normal cell count and no mestastases are present. The results of the procedure are periodically monitored utilizing the Blood CA 27,29 testing procedure.

Figure 3:
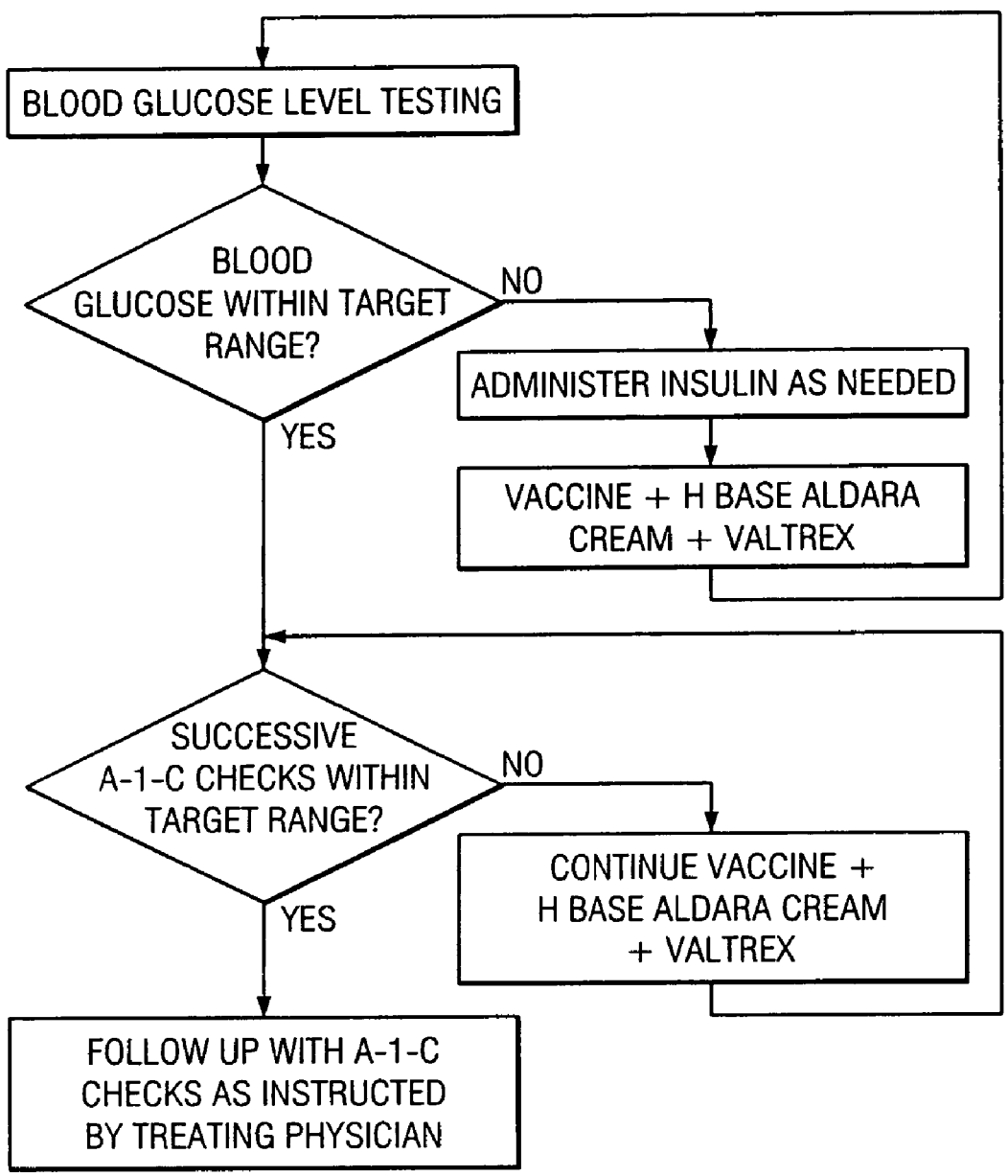
FIG. 3 is a flowchart illustrating the diabetes treatment method of the present invention.

Referring to FIG. 3 thereof, persons with Type I diabetes must check their blood glucose levels at multiple intervals as directed by their physician. The average fasting blood glucose level should be between 70 mg/dL and 110 mg/dL. If the blood glucose level is not within the target level, the level must be corrected by taking insulin.

The diabetes treatment procedure of the present invention comprises the transdermal administration of the drug imiquimod combined with a BCG vaccination and administration of valacyclovir hydrochiorine tablets. Imiquimod is commercially available from 3M Pharmaceuticals under the trademark ALDARA (TM) (imiquimod). A healthy human body produces the protein interferon alpha in response to an infection. Interferon alpha works to coat the infection or virus in order to make the infection or virus vulnerable to the human immune system. Imiquimod induces the production of interferon alpha once inside the human body, providing the needed interferon alpha not adequately produced by the patient's own body.

In accordance with the present invention, ALDARA (TM) (imiquimod) cream 5% is mixed at a 1:1 ratio with H base cream. The ingredients of H base cream are:

water, glycerin, canola oil, stearic acid, cetyl alcohol, PEG-100 stearate, glyceryl stearate, dimethicone, magnesium aluminum silicate, propylene glycol, triethanolamine, polysorbate 60, xanthan gum, bitter almond kernel oil, aloe vera, grape seed extract, wheat germ oil, vitamin E acetate, vitamin A palmitate, Vitamin C palmitate, tetrasodium EDTA, potassium sorbate, diazolidinyl urea. H base cream is a proprietary product produced by Professional Compounds Centers of America and licensed by it.

The mixture of imiquimod and H base cream as described above is administered transdermally, preferably by mixing ¼ cc ALDARA (TM) (imiquimod) 5% cream with ¼ cc H base cream and applying the resulting mixture to various locations, i.e., the inner thigh, abdomen, hip, arms, etc., of the patient. Various sites of administration prevent any possible skin irritation. The foregoing amount of the mixture of ALDARA (TM) (imiquimod) 5% cream and H base cream is applied daily.

Tumor necrosis factor (also called TNIFa, cachexin, or cachetin) stimulates T-cells that coordinate the immune system. In a healthy human body, tumor necrosis factor is released by white blood cells and other tissues in response to damage caused by an infection. Tumor necrosis factor is found in several vaccines. The preferable vaccine to be used in accordance with the present invention is the BCG vaccine, which is a common vaccine for tuberculosis, given in the United States and around the world. The tumor necrosis factor produced by the BCG vaccine and imiquimod work together to stimulate the T-cells and coordinate and improve the patient's immune system. Interferon alpha coats the virus or infection in order to make the virus or infection vulnerable to the tumor necrosis factor.

In accordance with the present invention, the vaccine is given in doses of 0.1 mL (100 µg) once every three weeks as long as the treatment continues. Valacyclovia hydrochlorine tablets, available from GlaxoSmithKline under the trademark VALTREX (TM) (valaevclovir) is a drug commonly used in the treatment for genital herpes. In accordance with the present invention, VALTREX (TM) (valacyclovir) tablets are consumed twice daily in 500 mg doses.

The results of the procedure are monitored utilizing blood sugar meters and a diary to record ongoing blood sugar levels. Additionally, A-1-C checks track the patient's overall blood sugar levels over two to three month periods, and is the most effective way to track long-range success of the treatment. The treatment method regenerates islet cells, which produce insulin. Once the patient no longer depends on insulin to correct blood sugar levels, the treatment continues until the patient has two or more sequential A-1-C checks in the target range, depending on the judgment of the treating physician. Once treatment is discontinued, A-1-C checks continue, but at less frequent intervals as recommended by the treating physician.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

The invention claimed is:

1. A method of treating duct cell breast cancer in a patient comprising the steps of: providing a quantity of ALDARA™ (imiquimod) 5% cream; providing a quantity of H base cream™; mixing ¼ cc. Of the ALDARA™ (imiquimod) 5% cream with ¼ cc. Of the H base cream™ and transdermally administering the resulting mixture, in conjunction with administering a BCG vaccine; and orally administering VALTREX™ (valacyclovir) tablets, to the patient.

2. The method of treating duct cell breast cancer according to claim 1 wherein the ALDARA (TM) (imiquimod) 5% cream/H base cream mixture is applied daily and the progress of the procedure is monitored using the Blood CA 27,29 testing procedure.

3. The method of treating duct cell breast cancer according to claim 1 wherein the BCG vaccine is administered every three weeks and 500 mg VALTREX (TM) (valacyclovir) tablets are orally administered twice daily.

4. The method of treating duct cell breast cancer according to claim 3 wherein the progress of the procedure is monitored using the Blood CA 27,29 testing procedure.

5. The method of treating duct cell breast cancer according to claim 2 wherein the Blood CA 27,29 testing procedure is administered prior to said treating, and treating is carried out if said testing procedure reveals the presence of duct cell breast cancer.

* * * * *

UNITED STATES PATENT AND TRADEMARK OFFICE
CERTIFICATE OF CORRECTION

PATENT NO. : 7,125,836 B2  Page 1 of 1
APPLICATION NO. : 11/133838
DATED : October 24, 2006
INVENTOR(S) : John. R. Woodward It is certified that error appears in the above-identified patent and that said Letters Patent is hereby corrected as shown below:

On Title page item 56
IN REFERENCES CITED

Col. 1, line 2, replace "GlaxoSmithKline)" with --GlaxoSmithKline--.

IN THE SPECIFICATION

Col. 2, line 9, replace "valacyclovir" with -- valacyclovia --.
Col. 3, line 28, replace "valacyclovir" with -- valacyclovia --.
Col. 3, line 29, replace "hydrochiorine tablets" with -- hydrochlorine tablets--.
Col. 4, line 35, replace "hydrochiorine tablets" with -- hydrochlorine tablets --.

IN THE CLAIMS

Claim 1, col. 6, line 12, replace "Of the ALDARA" with -- of the ALDARA --.
Claim 1, col. 6, line 13, replace "Of the H base" with -- of the H base--.
Claim 1, col. 6, line 15, replace "administering a BCG" with --administering BCG --.

Signed and Sealed this

Thirtieth Day of January, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,125,836 B2 | Page 1 of 1 |
| APPLICATION NO. | : 11/133838 | |
| DATED | : October 24, 2006 | |
| INVENTOR(S) | : John R. Woodward | |

It is certified that error appears in the above-identified patent and that said Letters Patent is hereby corrected as shown below:

On Title page item 56

IN REFERENCES CITED

Col. 1, line 2, replace "GlaxoSmithKline)" with --GlaxoSmithKline--.

IN THE SPECIFICATION

Col. 2, line 9, replace "valacyclovir" with -- valacyclovia --.
Col. 3, line 28, replace "valacyclovir" with -- valacyclovia --.
Col. 3, line 29, replace "hydrochiorine tablets" with -- hydrochlorine tablets--.
Col. 4, line 35, replace "hydrochiorine tablets" with -- hydrochlorine tablets --.

IN THE CLAIMS

Claim 1, col. 6, line 12, replace "Of the ALDARA" with -- of the ALDARA --.
Claim 1, col. 6, line 13, replace "Of the H base" with -- of the H base--.
Claim 1, col. 6, line 15, replace "administering a BCG" with --administering BCG --.

Signed and Sealed this

Twentieth Day of February, 2007

JON W. DUDAS
*Director of the United States Patent and Trademark Office*